United States Patent [19]
Rosen et al.

[11] Patent Number: 5,159,109

[45] Date of Patent: Oct. 27, 1992

[54] PURIFICATION OF ORGANIC POLYCARBOXYLIC ACIDS

[75] Inventors: Bruce I. Rosen, Morton Grove; David A. Peterson, Westmont, both of Ill.

[73] Assignee: Amoco Corporation, Chicago, Ill.

[21] Appl. No.: 657,451

[22] Filed: Feb. 19, 1991

Related U.S. Application Data

[62] Division of Ser. No. 555,765, Jun. 25, 1990.

[51] Int. Cl.$^5$ .............................................. C07C 61/09
[52] U.S. Cl. ..................................... 562/509; 562/486
[58] Field of Search ...................... 562/509, 486, 485

[56] References Cited

U.S. PATENT DOCUMENTS 3,835,167  9/1974  Pfister ................................. 260/351

FOREIGN PATENT DOCUMENTS 139977   2/1980  German Democratic Rep. .
53-21136 2/1978  Japan .
961062   6/1964  United Kingdom .

OTHER PUBLICATIONS

Vogel, "Practical Organic Chemistry," 3rd Ed, pp. 145-149 (1956).

Primary Examiner—Michael L. Shippen
Attorney, Agent, or Firm—Gunar J. Blumberg; William H. Magidson; Frank J. Sroka

[57] ABSTRACT

There is provided a method for purifying an organic polycarboxylic acid wherein the amounts of organic monofunctional impurities associated therewith are substantially reduced, which method comprises conducting steam distillation of a stream comprising said polycarboxylic acid. In one embodiment of the method, a reactor effluent comprising a polycarboxylic acid is introduced into a crystallization zone, said effluent being subjected to crystallization and steam distillation coextensively in said crystallization zone.

The method of the present invention may be used suitably to purify 1,4-cyclohexanedicarboxylic acid in a reactor effluent from the hydrogenation of a terephthalic acid by reducing the amounts of 4-methyl-1-cyclohexanecarboxylic acid and cyclohexanecarboxylic acid, as well as other organic impurities, contaminating the dicarboxylic acid.

There is also provided the polycarboxylic acid purified by the method of the present invention.

6 Claims, 3 Drawing Sheets

5,159,109

PURIFICATION OF ORGANIC POLYCARBOXYLIC ACIDS

This is a division of application Ser. No. 07/555,765, filed Jun. 25, 1990.

BACKGROUND OF THE INVENTION

1. Field of the Invention

The present invention relates to the purification of organic polycarboxylic acids by the removal therefrom of organic monofunctional impurities. More particularly, it relates to the purification of an organic polycarboxylic acid, such as 1,4-cyclohexanedicarboxylic acid, via steam distillation, wherein organic impurities, such as 4-methyl-1-cyclohexanecarboxylic acid and cyclohexanecarboxylic acid, are removed from the polycarboxylic acid.

2. Description of the Prior Art

In U.S. Pat. No. 3,243,456, Caldwell, et al, disclose a method for purifying insoluble dicarboxylic acids wherein insoluble acids are converted into any soluble salt, such as ammonium, sodium, lithium, potassium, or amine salts, by adding bases or basic salts to a suspension of the acid, the solutions of the salts of insoluble organic acids are treated with various absorbing agents, such as activated carbons, clays, and ion exchange resins and optionally with oxidizing agents or reducing agents to convert various impurities to substances which can be removed more easily than the original form, and the insoluble acid is regenerated by treating the hot solution of the salt with a soluble acid having an ionization constant which is lower than that of the insoluble acid which is being purified, which will cause the insoluble acid to form large, uniform crystals of pure acid.

In U.S. Pat. No. 3,646,124, Johnson, et al, disclose an extraction process for the removal of impurities from terephthalic acid wherein an aqueous solution of a salt of terephthalic acid is extracted with n-butanol or benzyl alcohol at a temperature of about 0° C. (32° F.) to about 150° C. (302° F.). The resulting phases are separated to provide an aqueous salt solution of increased purity, and the terephthalic acid is precipitated from solution by acidification.

In U.S. Pat. No. 3,746,750, Stautzenberger, et al, disclose a process for purifying relatively insoluble acids, such as terephthalic acid, by forming a solution of the acid in an aqueous solution of weak acid salts of lithium, a tertiary ammonium ion, or a quaternary ammonium ion, treating the resulting solution with a reagent, such as an oxidizing agent, to reduce the impurities that are present, and recrystallizing the purified acid from solution.

In U.S. Pat. No. 4,500,732, Petty-Weeks, et al, disclose a process for removing p-toluic acid from purified terephthalic acid, wherein p-toluic acid is extracted from the aqueous terephthalic acid-water phase with p-xylene, and the p-toluic acid and p-xylene are recycled to the p-xylene oxidation reactor.

Now there has been developed a process for the purification of organic polycarboxylic acids that are immiscible or partially miscible with water, which process employs steam distillation.

SUMMARY OF THE INVENTION

According to the present invention, there is provided a method for purifying an organic polycarboxylic acid which contains organic impurities and which is immiscible or partially miscible with water. In one embodiment, the method comprises passing a stream comprising water, said impurities, and said polycarboxylic acid into a purification zone and conducting steam distillation in said zone to produce a purified polycarboxylic acid containing a reduced amount of said impurities and a vapor phase comprising water and at least a portion of said impurities, withdrawing said vapor phase from said zone as overhead, cooling said overhead to form a condensate, separating said condensate into a layer of water from said condensate and a layer of the organic impurities from said condensate, optionally recycling at least a portion of said layer of water to said zone, and withdrawing said pure polycarboxylic acid from said zone.

In a second embodiment, the method comprises passing from a reaction zone an effluent comprising an organic polycarboxylic acid, organic impurities, and water into a crystallization zone at a temperature which is sufficiently low to permit crystals of the purified polycarboxylic acid containing a reduced amount of said impurities to form and yet sufficiently high to enable water and said impurities to be present in a vapor phase, conducting coextensively in said crystallization zone crystallization of said polycarboxylic acid and steam distillation, said crystallization producing a slurry comprising crystals of said polycarboxylic acid, said steam distillation producing water and said impurities in the vapor phase, withdrawing said vapor phase from said crystallization zone as overhead, cooling said overhead to form a condensate, separating said condensate into a layer of water and a layer of said impurities, optionally recycling said layer of water to said crystallization zone, withdrawing from said crystallization zone said slurry, separating said slurry into a mother liquor and said crystals, recycling at least a portion of said mother liquor to said reaction zone or to said crystallization zone, and recovering said crystals as purified organic polycarboxylic acid.

In a specific embodiment, the method of the present invention can be used to remove the impurities 4-methyl-1-cyclohexanecarboxylic acid and cyclohexanecarboxylic acid from 1,4-cyclohexanedicarboxylic acid.

According to the present invention, there is provided also the polycarboxylic acid that is purified by the method of the present invention.

BRIEF DESCRIPTION OF THE INVENTION

Three Figures are appended hereto.

In each of the above simplified schematic diagrams, some pieces of auxiliary equipment, such as pumps, compressors, and heat exchangers, are not shown. However, one skilled in the art would recognize easily where such equipment would be located and when they would be used.

Figure 3:
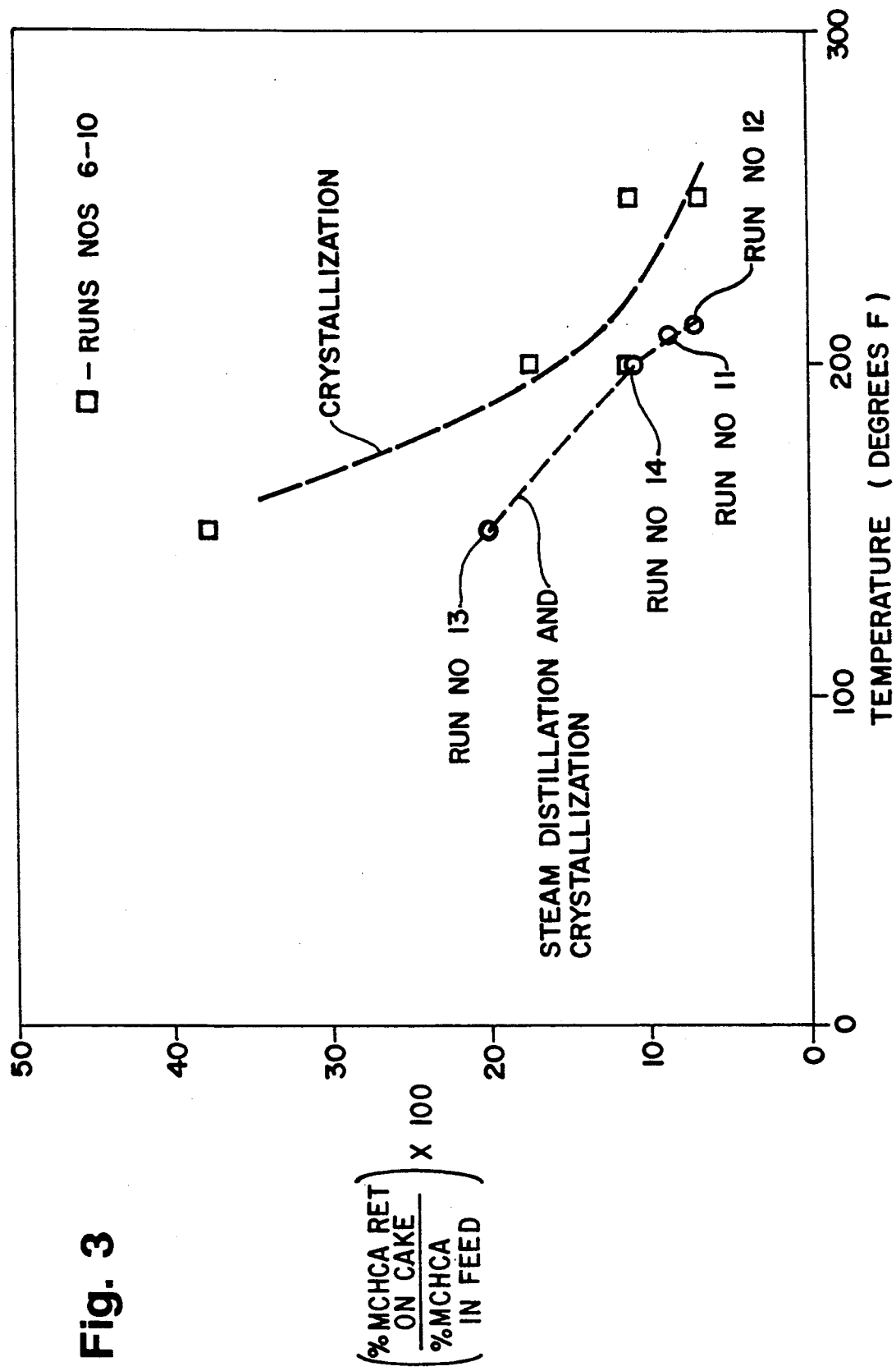

FIG. 3 presents a comparison of data obtained when only crystallization is employed to remove monofunctional impurities to data obtained when both crystallization and steam distillation are employed for the same purpose.

DESCRIPTION AND PREFERRED EMBODIMENTS

Often organic polycarboxylic acids are contaminated with monofunctional carboxylic acids. For example, the product stream obtained when terephthalic acid is hydrogenated to 1,4-cyclohexanedicarboxylic acid contains as impurities cis- and trans- 4-methyl-1-cyclohexanecarboxylic acid and cyclohexanecarboxylic acid. Such hydrogenated ring dicarboxylic acids as 1,4-cyclohexanedicarboxylic acid have potential applications in the preparation of novel polymers. However, the impurities affect detrimentally polymer molecular weight. Consequently, if they are to be used for polymer applications, the monomers should be of high purity in order to provide control of molecular weight. The organic impurities should be reduced substantially in quantity.

There has now been developed a method for the purification of organic polycarboxylic acids, such as 1,4-cyclohexanedicarboxylic acid, which method uses steam distillation.

Steam distillation is a technique wherein water (as steam) is added intentionally to a distilling organic mixture to reduce the required distillation temperature and to keep solids suspended. Steam distillation consists of distilling a mixture of water and an immiscible or partially miscible organic material. The overhead vapor will condense into two phases or layers. Consequently, the steam distillation system can be represented as a type of azeotropic distillation where water (or steam) is the added solvent and volatiles are separated from non-volatiles. The advantage of steam distillation is that it permits a mixture to be distilled below the boiling point of the lower-boiling component. As a result, a high-boiling organic compound in an aqueous environment can be removed well below its boiling point without the necessity of a vacuum. Steam distillation is currently used for removing of solvents from solids in waste disposal, for purification of oils in the perfume industry, and for distillations of hydrocarbons.

In the case of purifying an organic polycarboxylic acid via steam distillation, both the water and the organic phases exert their own vapor pressures. At atmospheric pressure the boiling point must be less than 100° C. (212° F.), the boiling point of the lower-boiling component, water, even though the monofunctional impurities have much higher boiling points. With both phases present and presumably in equilibrium, their compositions will be determined by their mutual solubilities. Since each phase exerts its own vapor pressure, the vapor composition will be constant regardless of the average liquid concentration. Essentially, a heterogeneous azeotrope is formed. As the amount of water or organic is increased, the phase concentrations do not change, only the amount of each liquid phase will change. Since an azeotrope has been attained, no additional separation is obtained by adding additional stages to the distillation vessel. As a result, a reboiler is the only necessary piece of equipment. In various embodiments of the method of the present invention, the crystallizer acts as a reboiler.

It is contemplated that such polycarboxylic acids as 1,4-cyclohexanedicarboxylic acid, terephthalic acid, isophthalic acid, and phthalic acid may be purified by the methods of the present invention.

According to the present invention, there is provided a method for purifying an organic polycarboxylic acid which contains organic impurities and which is immiscible or partially miscible with water, which method comprises passing a stream comprising water, said impurities, and said polycarboxylic acid into a purification zone and conducting steam distillation in said zone to produce a purified polycarboxylic acid containing a reduced amount of said impurities and a vapor phase comprising water and at least a portion of said impurities, withdrawing said vapor phase from said zone as overhead, cooling said overhead to form a condensate, separating said condensate into a layer of water and a layer of impurities, recycling at least a portion of said layer of water to said zone, and withdrawing said purified polycarboxylic acid from said zone.

It is contemplated that the purification zone may comprise a distillation column or a crystallizer. Since, as pointed out hereinabove, steam distillation is involved and only a reboiler is required, the vessel, whether a column or crystallizer, will act as a reboiler. Pursuant to steam distillation, the volatiles, i.e., water and the impurities, will be separated from the non-volatiles, i.e., the polycarboxylic acid. The purified polycarboxylic acid is the polcarboxylic acid containing an amount of the impurities that is reduced over the amount of impurities in the original polycarboxylic acid. The more efficient that the steam distillation is, the greater is the reduction of impurities.

A portion of the layer of water that is formed from condensate may be recycled optionally to the purification zone. Such recycling will be governed by the resulting economics of the selected embodiment of the method.

According to the present invention, there is provided a method for purifying an organic polycarboxylic acid which is immiscible or partially miscible with water and which is present in the reaction effluent from the reaction zone wherein it has been produced, said effluent comprising said organic polycarboxylic acid, organic impurities, and water, which method comprises passing said effluent into a crystallization zone at a temperature which is sufficiently low to permit crystals of the purified polycarboxylic acid containing a reduced amount of said impurities to form and yet sufficiently high to enable water and at least a portion of said impurities to be present in a vapor phase, conducting coextensively in said crystallization zone crystallization and steam distillation, said crystallization producing a slurry comprising said crystals and a mother liquor and said steam distillation producing said vapor phase comprising water and at least a portion of said impurities, withdrawing said vapor phase from said crystallization zone as overhead, cooling said overhead to form a condensate, separating said condensate into a layer of water and a layer of impurities, optionally recycling at least a portion of said layer of water to said crystallization zone, withdrawing said slurry from said crystallization zone, separating said slurry into said mother liquor and said crystals, recycling at least a portion of said mother liquor to said reaction zone or said crystallization zone, and recovering said crystals.

In this embodiment of the method of the present invention, the purification zone is made up of a crystallization zone in which crystallization and steam distillation occur coextensively.

The crystallization zone is made up of a single stage, which is operated at a temperature which is sufficiently low to permit crystals of the purified polycarboxylic acid to form and yet sufficiently high to permit water and the organic impurities to be in a vapor phase. Typically, the crystallization zone will be maintained at a temperature within the range of about 66° C. (150° F.) to about 120° C. (248° F.) and a pressure within the range of about 101 kPa (0 psig) to about 198 kPa (14 psig). Preferably, the crystallization zone will be operated at a temperature within the range of about 88° C. (190° F.) to about 110° C. (230° F.) and a pressure within the range of about 101 kPa (0 psig) to about 143 kPa (6 psig).

Figure 1:
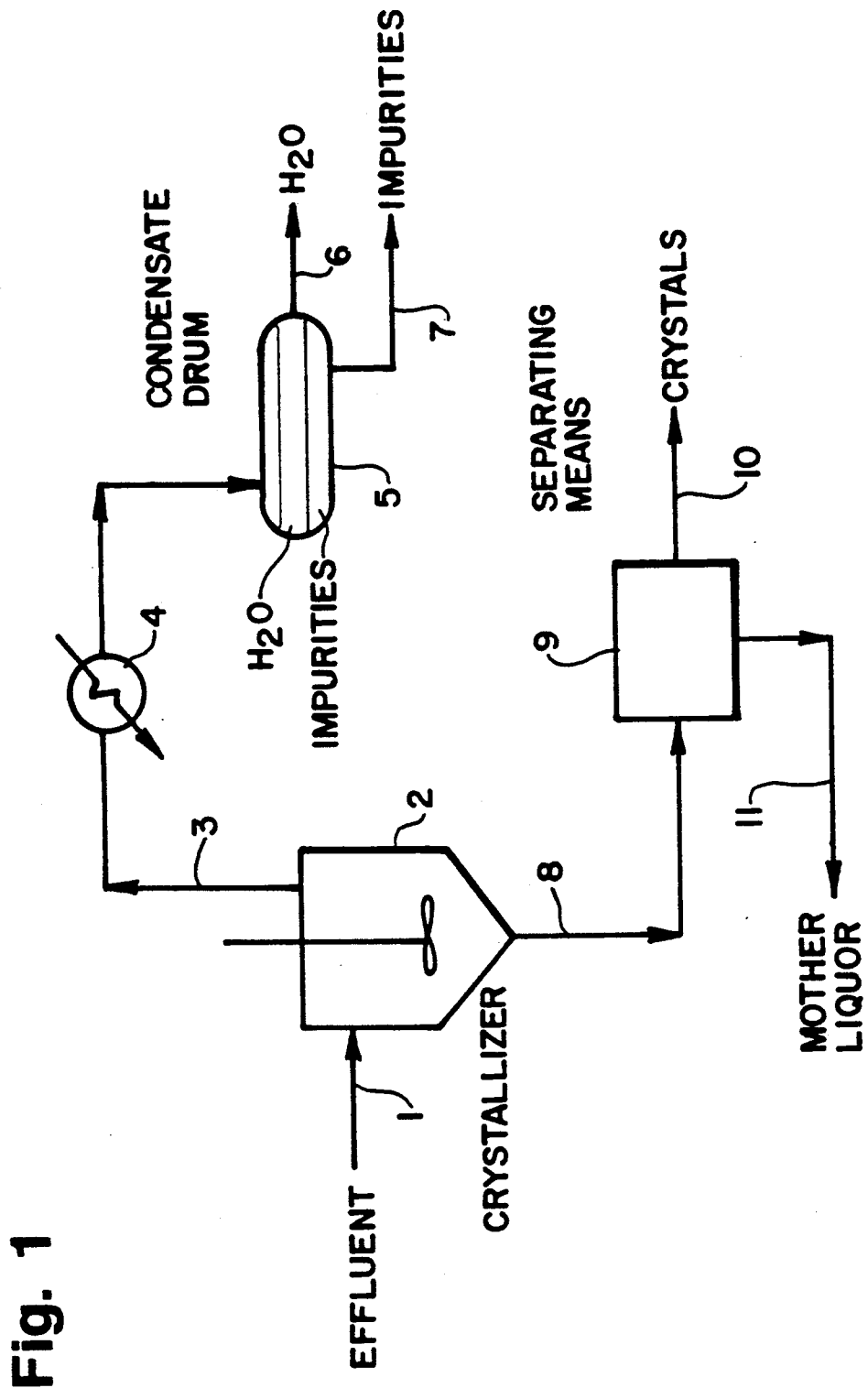
FIG. 1 is a simplified schematic diagram depicting a single-stage embodiment of the method of the present invention.

This embodiment is depicted in the simplified schematic diagram FIG. 1.

Referring to FIG. 1, an effluent from a reactor in which the desired polycarboxylic acid is produced passes through line 1 into crystallizer 2, where both crystallization and steam distillation occur. This reactor effluent comprises the polycarboxylic acid to be purified, water, and organic impurities. The temperature of the effluent is such that both the polycarboxylic acid and the organic monofunctional impurities are in solution. The temperature and pressure in crystallizer 2 are within the ranges provided hereinabove for this embodiment of the method of the present invention. Crystals of the polycarboxylic acid form while water and at least a portion of the impurities become vapor.

The vapor phase produced in crystallizer 2 passes as overhead through line 3 and condenser 4 into condensate drum 5. This vapor phase, comprising water and at least a portion of the organic impurities from the effluent, becomes condensate when cooled in condenser 4 and separates into a water layer and a layer of impurities in drum 5. The water layer passes from drum 5 via line 6 and may be recycled optionally to crystallizer 2, while the layer of impurities passes from drum 5 via line 7.

A product slurry, resulting from the crystallization of the polycarboxylic acid, passes from crystallizer 2 through line 8 into separating means 9, wherein the crystals of the polycarboxylic acid are separated from a mother liquor comprising polycarboxylic acid, water, and impurities. The separating means may be conveniently either a centrifuge or a filter. The crystals of purified polycarboxylic acid, i.e., polycarboxylic acid containing less impurities than the polycarboxylic acid in the reactor effluent, pass from the separating means 9 via line 10, while the mother liquor passes from separating means 9 via line 11 for recycle to either the reactor (not shown) or crystallizer 2. Preferably, recycle of the mother liquor is to the reactor.

There is also provided an embodiment of the method of the present invention wherein two stages of crystallization-steam distillation and separating means are employed. According to the present invention, this embodiment is a method for purifying 1,4-cyclohexanedicarboxylic acid in an effluent from a reactor wherein purified terephthalic acid is hydrogenated to produce said 1,4-cyclohexanedicarboxylic acid, said effluent comprising said 1,4-cyclohexanedicarboxylic acid, said terephthalic acid, organic impurities comprising at least one of 4-methyl-1-cyclohexanecarboxylic acid and cyclohexanecarboxylic acid, and water, which method comprises passing said effluent into a first crystallizer, said first crystallizer being operated at a temperature that is sufficiently low to permit the formation of crystals of said purified terephthalic acid and yet sufficiently high to permit the formation of a first vapor phase comprising water and at least a portion of said impurities, conducting coextensively in said first crystallizer a first crystallization and first steam distillation, said first crystallization producing a first slurry comprising said crystals of said purified terephthalic acid and a first mother liquor comprising water, 1,4-cyclohexanedicarboxylic acid, and at least a portion of said impurities and said first steam distillation producing said first vapor phase comprising water and at least a portion of said impurities, withdrawing said first vapor phase from said first crystallizer as a first overhead, cooling said first overhead to form a first condensate, separating said first condensate into a first water layer and a first layer of impurities, optionally recycling at least a portion of said first water layer to said first crystallizer, withdrawing said first slurry from said first crystallizer, separating in a first separating means said first slurry into said first mother liquor and said crystals of purified terephthalic acid, passing said first mother liquor into a second crystallizer, said second crystallizer being operated at a temperature that is sufficiently low to permit the formation of crystals of purified 1,4-cyclohexanedicarboxylic acid containing a reduced amount of said impurities and yet sufficiently high to permit the formation of a second vapor phase comprising water and at least a portion of said impurities, conducting coextensively in said second crystallizer a second crystallization and second steam distillation, said second crystallization producing a second slurry comprising said crystals of purified 1,4-cyclohexanedicarboxylic acid and a second mother liquor comprising water and a portion of said impurities and said second steam distillation producing said second vapor phase comprising water and at least a portion of said impurities, withdrawing said second vapor phase from said second crystallizer as a second overhead, cooling said second overhead to form a second condensate, separating said second condensate into a second water layer and a second layer of impurities, optionally recycling at least a portion of said second water layer to said second crystallizer, withdrawing said second slurry from said second crystallizer, separating in a second separating means said second slurry into said second mother liquor and said crystals of purified 1,4-cyclohexanedicarboxylic acid, recycling at least a portion of said second mother liquor to said reactor or said second crystallizer, and recovering said crystals of purified 1,4-cyclohexanedicarboxylic acid.

In this latter embodiment, 1,4-cyclohexanedicarboxylic acid is the polycarboxylic acid that is purified. Its precursor, purified terephthalic acid, provides a crystallization temperature that is greater than that of 1,4-cyclohexanedicarboxylic acid.

Figure 2:
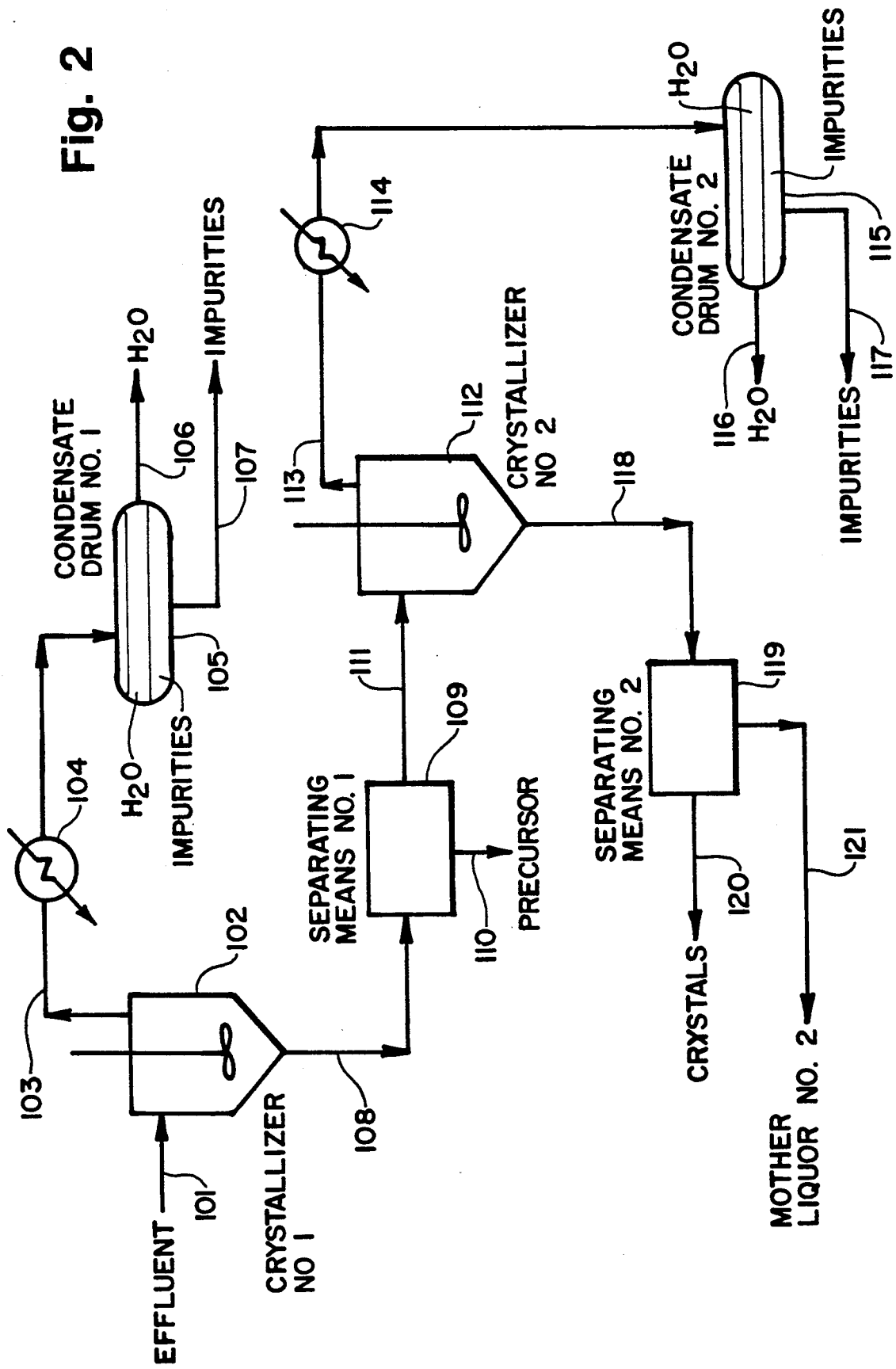
FIG. 2 is a simplified schematic diagram representing a two-stage embodiment of the method of the present invention.

This latter embodiment is represented by the simplified schematic diagram in FIG. 2. It is contemplated that any polycarboxylic acid the precursor of which has a crystallization temperature that is greater than the crystallization temperature of the polycarboxylic acid may be purified by the embodiment that is depicted in simplified schematic diagram FIG. 2. In view of this, FIG. 2 is described hereinafter in terms of "polycarboxylic acid," rather than in terms of the specific 1,4-cyclohexanedicarboxylic acid.

Referring to FIG. 2, reactor effluent comprising water, the impure polycarboxylic acid, any precursor of said polycarboxylic acid, and organic impurities pass via line 101 into crystallizer 102 (Crystallizer No 1), wherein both crystallization and steam distillation occur coextensively. The reactor effluent is at a temperature which will permit all principal ingredients thereof to be in solution. This crystallizer 102 is operated at a temperature which is sufficiently low to permit any crystals of the precursor of the desired polycarboxylic acid to form, but not low enough to permit crystals of the polycarboxylic acid to form, and yet sufficiently high to permit water and at least a portion of the organic impurities to vaporize. Typically, crystallizer 102 (Crystallizer No 1) will be maintained at a temperature within the range of about 120° C. (248° F.) to about 260° C. (500° F.) and a pressure within the range of about 198 kPa (14 psig) to about 4,693 kPa (666 psig). Preferably, crystallizer 102 will be operated at a temperature within the range of about 120° C. (248° F.) to about 177° C. (350° F.) and a pressure within the range of about 198 kPa (14 psig) to about 901 kPa (116 psig). Crystals of the precursor form and water and at least a portion of the organic impurities vaporize. The desired polycarboxylic acid remains in solution.

The vapor comprising water and impurities passes as overhead from crystallizer 102 via line 103 and condenser 104 into condensate drum 105 (Condensate Drum No 1). This vapor becomes condensate when cooled in condenser 104 and separates into a layer of water and a layer of impurities in condensate drum 105. The water layer passes from drum 105 via line 106 and may be recycled, if desired, to crystallizer 102, while the layer of impurities passes from drum 105 via line 107.

The product slurry, resulting from the crystallization of the precursor of the polycarboxylic acid and comprising crystals of said precursor and a Mother Liquor No 1, passes from crystallizer 102 via line 108 into separating means 109 (Separating Means No 1), wherein the crystals of precursor separate from the Mother Liquor No 1, which comprises water, polycarboxylic acid, and impurities. Conveniently, the separating means 109 may be either a centrifuge or a filter. The crystals of precursor, typically in the form of a cake, are removed from separating means 109, as indicated by arrow 110, and may be recycled to the reactor (not shown). Mother Liquor No 1 passes from separating means 109 via line 111 to crystallizer 112 (Crystallizer No 2), wherein crystallization and steam distillation occur coextensively. Crystallizer 112 is operated at a temperature which is sufficiently low to permit crystals of the desired polycarboxylic acid to form and yet sufficiently high to permit water and at least a portion of remaining impurities to be in a vapor phase. Typically, crystallizer 112 (Crystallizer No 2) will be maintained at a temperature within the range of about 66° C. (150° F.) to about 120° C. (248° F.) and a pressure within the range of about 101 kPa (0 psig) to about 198 kPa (14 psig). Preferably, crystallizer 112 will be operated at a temperature within the range of about 88° C. (190° F.) to about 110° C. (230° F.) and a pressure within the range of about 101 kPa (0 psig) to about 143 kPa (6 psig).

The vapor phase in crystallizer 112 (Crystallizer No 2) passes as overhead through line 113 and condenser 114 into condensate drum 115 (Condensate Drum No 2). This vapor phase, comprising water and at least a portion of the organic impurities becomes condensate when cooled in condenser 114 and separates into a layer of water and a layer of impurities in drum 115. The layer of water passes from drum 115 via line 116 and may be recycled, if desired, to crystallizer 112, while the layer of impurities passes from drum 115 by way of line 117.

A product slurry, comprising crystals of purified polycarboxylic acid containing a reduced amount of organic impurities and a mother liquor (Mother Liquor No 2) comprising water, polycarboxylic acid, and some of said impurities, passes from crystallizer 112 (Crystallizer No 2) through line 118 into separating means 119 (Separating Means No 2), wherein the crystals of the purified polycarboxylic acid are separated from Mother Liquor No 2. The Separating Means No 2 may be either a centrifuge or a filter. The crystals of purified polycarboxylic acid are withdrawn from Separating Means No 2 as represented by arrow 120 and Mother Liquor No 2 passes from Separating Means No 2 via line 121 to be recycled to either the reactor (not shown) or Crystallizer No 2. It is preferred that the Mother Liquor No 2 be recycled to the reactor.

According to the present invention, there are provided the polycarboxylic acids that are purified by the method described hereinabove.

The following examples are presented hereinafter to facilitate an understanding of the method of the present invention. They are presented for the purposes of illustration only and are not intended to limit the scope of the present invention.

EXPERIMENTAL

For the following examples, crystallizations were performed in a one-gallon, titanium-lined autoclave equipped with a filter and a drain line to a stainless steel-lined receiver. Steam distillations were conducted in typical laboratory glassware. One-step steam distillation/crystallizations were performed in a one-gallon autoclave that had been modified with an overhead condenser which allowed for removal of condensate. In this case, make-up water was added by way of a wash bomb.

A synthetic reactor effluent (feed mixture) was used in these examples unless otherwise specified. This mixture was made up of 380 gm of 1,4-cyclohexanedicarboxylic acid (identified as CHDA or 1,4-CHDA), 20 gm of 4-methyl-1-cyclohexanecarboxylic acid (MCHCA), and 1,200 gm of water. The CHDA was obtained from Eastman Chemicals Company and the MCHCA was obtained from Aldrich Chemical Company. The compositions of these materials are given hereinbelow in Table I.

TABLE I

| COMPOSITION OF FEED MATERIALS[1] | | | | | | |
|---|---|---|---|---|---|---|
| | MCHCA | | CHDA | | OTHERS[2] | | |
| | cis | trans | cis | trans | TA | p-Tol | HMBA |
| CHDA | — | — | 57.8 | 42.2 | — | — | trace |
| MCHCA | 59.41 | 40.35 | — | — | 0.01 | 0.23 | — |

[1]By HPLC analysis
[2]TA = terephthalic acid
p-Tol = p-toluic acid
HMBA = hydroxymethyl benzoic acid The mixture was heated for 2 hr. at a temperature of 225° C. (437° F.), cooled to the desired crystallization temperature and filtered. The filter cake was washed once with 500 gm of water and analyzed by high performance liquid chromatography (HPLC).

Separation factors were defined as:

(% MCHCA retained on cake)/(% MCHCA in feed).

All calculations were based on HPLC data. Samples for analysis were dissolved and diluted with 4N ammonium hydroxide. Optimum peak clarity was obtained with 0.15 gm solid in 100 ml liquid within a pH range of 9 to 10. The diluted sample was injected onto an Alltech Spherisorb ODS-1 5μ column at 50° C. (122° F.). The gradient system consisted of 0.5% methylphosphoric acid in distilled and deionized water and 99.9% HPLC-grade acetonitrile obtained from Aldrich Chemical Co. Detection was performed with an UV absorbance Shimadzu detector at 220 nm. The delivery system, pump, and autosampler were manufactured by Spectra Physics with LABNET interface. Integration was handled with the VAX Multichrom data acquisition system.

EXAMPLE 1

Two tests were conducted to demonstrate that MCHCA could be removed from the synthetic feed mixture via steam distillation. In each run, a mixture of CHDA, MCHCA, and water was flash distilled with the resulting pot residue and distillate being analyzed by HPLC. The results of these runs, Run No 1 and Run No 2, are presented hereinafter in Table II.

TABLE II

STEAM DISTILLATION TRIALS - PRODUCT COMPOSITIONS BY HPLC

| | $H_2O$, gm | t-CHDA, gm | c-CHDA, gm | c-MCHCA, gm | t-MCHCA, gm |
|---|---|---|---|---|---|
| Run No 1 | | | | | |
| Feed | 71.4 | 9.1 | 10.0 | 4.7 | c/t mix |
| Pot residue[1] | 22.3 | 7.41 | 9.43 | 1.86 | 0.65 |
| Distillate | 52.6 | 0.03 | 0.04 | 0.63 | 0.26 |
| Run No 2 | | | | | |
| Feed | 70.9 | 9.3 | 9.6 | 2.6 | c/t mix |
| Pot residue[1] | 7.65 | 10.35 | 12.46 | 1.04 | 0.21 |
| Clear distillate[2] | 53.77 | 0.00 | 0.09 | 0.09 | 0.05 |
| White distillate[3] | 4.67 | 0.15 | 0.28 | 1.10 | 0.05 |

[1]Weight determined by difference of feed and distillate
[2]Water layer
[3]Organic layer Although the mass balances as determined by HPLC were only fair, qualitatively, the results indicated that the MCHCA could be removed from the synthetic reactor effluent by means of steam distillation with relatively little loss of the desired CHDA.

EXAMPLE 2

In this example, Run No 3, a follow-up experiment to Example 1, the feed mixture of Example 1 was distilled in a 10-tray Oldershaw column (reflux ratio=1; pot temperature=103° C.; head temperature=99°-100° C.) in an attempt to improve the separation of MCHCA from the less volatile CHDA. The organic fraction of this steam distillation contained 66.5% cis-MCHCA, 33.4% trans-MCHCA, and 0.024% other material, as shown by HPLC.

Approximately 95 ml of distillate were collected with the organic fraction containing about 3 ml. The HPLC results indicated that the organic fraction contained only MCHCA and a small amount of impurities present in the starting material.

EXAMPLE 3

In this example, a synthetic reactor effluent was distilled in a 5-tray Oldershaw column (reflux ratio=1, pot temperature=103° C., head temperature=99°-100° C.). Eight fractions were collected (approximately 100 ml each) with concomitant replacement of the water. The results of this run, Run No 4, are presented hereinbelow in Table III.

The product analyses indicated that: (1) the condensate (both organic and water) contained essentially no CHDA; (2) the concentration of the MCHCA in the water layer of the overhead condensate was less than 0.4%; and (3) the cis-to-trans ratio of the MCHCA in the condensate changed with time. Approximately 0.54 gm of organic condensate was from the water layer. Approximately 5.56 gm of MCHCA were removed (2.11 gm in the water layer and 3.45 gm in the organic layer) by about 781 gm of water (140 gm of water per gm of MCHCA removed). Consequently, about 56% of the volatile impurities were removed by this steam distillation.

TABLE III

STEAM DISTILLATION - 5-TRAY OLDERSHAW COLUMN RUN NO. 4

| | Normalized | | | | | | Weight, gm | | | | | |
|---|---|---|---|---|---|---|---|---|---|---|---|---|
| | MCHCA | | 1,4-CHDA | | | | MCHCA | | 1,4-CHDA | | | |
| | cis | trans | cis | trans | p-Tol | Others | cis | trans | cis | trans | p-TOL | Others |
| Water Layer - | 68.20 | 31.79 | — | — | 0.01 | — | 0.16 | 0.07 | — | — | — | — |
| Condensate | 67.03 | 32.82 | — | — | 0.01 | 0.15 | 0.14 | 0.07 | — | — | — | — |
| | 66.04 | 33.93 | — | 0.02 | 0.01 | — | 0.11 | 0.05 | — | — | — | — |
| | 65.39 | 34.60 | — | — | 0.01 | — | 0.11 | 0.06 | — | — | — | — |
| | 65.69 | 34.30 | — | — | 0.01 | — | 0.11 | 0.05 | — | — | — | — |
| | 65.24 | 34.61 | — | — | 0.01 | 0.14 | 0.19 | 0.10 | — | — | — | — |
| | 62.83 | 36.99 | — | — | 0.02 | 0.16 | 0.12 | 0.07 | — | — | — | — |
| | 61.90 | 36.08 | — | — | 0.02 | — | 0.12 | 0.07 | — | — | — | — |
| Organic Layer - | 69.06 | 30.93 | — | — | 0.01 | trace | 0.30 | 0.13 | — | — | — | — |
| Condensate | 68.65 | 31.34 | — | — | — | 0.01 | 0.56 | 0.25 | — | — | — | — |
| | 67.81 | 32.16 | — | — | 0.01 | 0.02 | 0.52 | 0.24 | — | — | — | — |
| | 67.22 | 32.77 | — | — | — | 0.01 | 0.45 | 0.21 | — | — | — | — |
| | 67.73 | 32.26 | — | — | 0.01 | 0.01 | 0.43 | 0.20 | — | — | — | — |
| | 65.73 | 34.26 | — | — | 0.01 | trace | 0.22 | 0.11 | — | — | — | — |
| | 64.12 | 35.86 | — | — | 0.01 | 0.01 | 0.15 | 0.08 | — | — | — | — |
| | 62.47 | 37.37 | — | 0.13 | 0.01 | 0.03 | 0.09 | 0.05 | — | — | — | — |
| Reboiler | 0.65 | 1.06 | 56.01 | 42.28 | 0.01 | 0.01 | 1.27 | 2.01 | 109.40 | 82.77 | 0.01 | — |
| Starting Material | | | | | | | 5.91 | 4.01 | 109.85 | 80.20 | 0.02 | — |
| Total 1,4-CHDA Recovery | | | 101% | | | | | | | | | |
| Total MCHCA Recovery | | | 89% | | | | | | | | | |

EXAMPLE 4

In this example, crystallizations of the synthetic reactor effluent were performed at crystallization temperatures of 149° C. (300° F.), 121° C. (250° F.), 93° C. (200° F.), and 66° C. (150° F.). This reactor effluent had a cis-to-trans ratio for CHDA of 57/43 and a cis-to-trans ratio for MCHCA of 60/40. The filter cake was washed with approximately 500 gm of water and was dried in air at room temperature overnight.

The various cake compositions as determined by HPLC analysis are listed hereinafter in Table IV. The crystallization attempted at 149° C. (300° F.), in Run No 5, resulted in no cake being isolated. When the temperature was lowered to 121° C. (250° F.) in Run No 6 and Run No 7, about 75 to 95 gm of cake were isolated. This cake had a composition that was greater than 99% CHDA (almost 99% trans-isomer) and less than 0.6% trans-MCHCA (no cis isomer was detected). As the crystallization temperature was further lowered to 93° C. (200° F.) in Run No 8 and Run No 9, the weight of cake increased to about 150 gm. Although the CHDA content was still greater than 99%, MCHCA content had increased to about 0.9%. At a crystallization temperature of 66° C. (150° F.) in Run No 10, the weight of cake was 200 gm, with a cake composition of 98% CHDA and slightly less than 2% MCHCA.

once at a temperature of 98° C. (209° F.) with 500 ml of water. The filter cake from this run, Run No 11, was found to contain 0.46% trans-MCHCA, 1.07% cis-1,4-CHDA, 98.4% trans-1,4-CHDA, 0.02% terephthalic acid, and 0.07% HMBA. These results indicated that the cake was quite pure.

In addition, a test, Run No 12, was conducted in an autoclave that had been modified to allow for removal of overhead condensate and the water used in the condensation was replaced via a wash bomb.

In this run, Run No 12, steam distillation purge of MCHCA at a temperature of 149° C. (300° F.) followed by crystallization at 100° C. (212° F.) was performed on synthetic reactor effluent having a CHDA cis-to-trans ratio of 1.37. The results of this test are presented hereinafter in Table V.

Total mass accountability for this run, Run No 12 was 94% (condensate, filter cake, and mother liquor). Approximately 380 gm of water were needed to remove 3.4 gm of MCHCA (starting cis-to-trans ratio of 1.47) in the overhead. The filter cake contained about 131 gm of CHDA and 0.5 gm of MCHCA, while the mother liquor contained 221 gm of CHDA and 16 gm of MCHCA. Some isomerization did occur. The cis-to-trans ratio of CHDA changed from 1.37 to 0.86 and the cis-to-trans ratio of MCHCA changed from 1.47 to 0.99. The data indicate that the cake purity is better than that

TABLE IV
EFFECT OF CRYSTALLIZATION TEMPERATURE UPON FILTER CAKE COMPOSITION

| | | | Cake Composition[1] | | | | | | | |
|---|---|---|---|---|---|---|---|---|---|---|
| | Crystallization | Cake Wt. (Dry), | MCHCA | | 1,4-CHDA | | Others | | | |
| Run No. | Temp. °F. | gm | cis | trans | cis | trans | TA | p-Tol | HMBA | UnK |
| 5 | 300 | 0 | — | — | — | — | — | — | — | — |
| 6 | 250 | 95 | — | 0.35 | 1.03 | 98.6 | 0.02 | — | 0.04 | — |
| 7 | 250 | 77 | — | trace[2] | 1.69 | 98.3 | 0.01 | — | 0.02 | — |
| 8 | 200 | 147 | — | 0.57 | 1.01 | 98.4 | 0.01 | — | 0.03 | — |
| 9 | 200 | 154 | — | 0.85 | 1.10 | 98.0 | 0.02 | — | 0.02 | — |
| 10 | 150 | 203 | — | 1.88 | 1.10 | 97.0 | 0.03 | — | 0.01 | — |

[1]HPLC Analyses normalized to 100%. Analysis performed on wet cake.
[2]Dry cake analysis indicated 0.56% trans-MCHCA present.

EXAMPLE 5

In an attempt to demonstrate the combined effects of steam distillation and crystallization on product purity, the pot residue from Run No 3 (steam distillation in the 10-tray Oldershaw column) was placed in the autoclave, heated to 225° C. (437° F.) for 2 hr, cooled to 98° C. (209° F.), filtered, and the resulting cake was washed obtained at a similar crystallization temperature without steam distillation.

TABLE V
STEAM DISTILLATION AT 149° C. (300° F.) AND CRYSTALLIZATION AT 100° C. (212° F.)
RUN NO. 12

| | Normalized | | | | | Weight Percent | | | | | Weight, gm | | | | |
|---|---|---|---|---|---|---|---|---|---|---|---|---|---|---|---|
| | MCHCA | | 1,4-CHDA | | | MCHCA | | 1,4-CHDA | | | MCHCA | | 1,4-CHDA | | |
| | cis | trans | cis | trans | Others | cis | trans | cis | trans | Water | cis | trans | cis | trans | Water |
| Condensate | 58.0 | 40.77 | 0.78 | 0.40 | 0.05 | 0.529 | 0.359 | 0.007 | 0.004 | 99.1 | 2.02 | 1.37 | 0.03 | 0.02 | 378.78 |
| Filter Cake | — | 0.35 | 1.31 | 98.30 | 0.04 | — | — | 1.01 | 76.26 | 22.7 | — | 0.47 | 1.71 | 129.35 | 38.63 |
| Mother Liquor | 3.23 | 3.48 | 67.81 | 25.44 | 0.05 | 0.43 | 0.45 | 8.99 | 3.39 | 86.73 | 7.76 | 8.07 | 161.15 | 60.83 | 1554.28 |
| Totals | | | | | | | | | | | 9.78 | 9.91 | 162.89 | 190.20 | 1971.69 |
| Starting Materials | | | | | | | | | | | 11.7 | 27.96 | 219.66 | 160.36 | 2101.72 |
| Total Recovery | 93.7% | | | | | | | | | | | | | | |
| Total 1,4-CHDA Recovery | 92.9% | | | | | | | | | | | | | | |
| Total MCHCA Recovery | 100.0% | | | | | | | | | | | | | | |
| Total H$_2$O Recovery | 93.8% | | | | | | | | | | | | | | |

EXAMPLE 6

In this example, a run, Run No 13, was conducted in which about 550 gm of condensate from Run No 4 were used as part of the reaction mixture. This condensate contained at least 1.4 gm of MCHCA. The remainder of the feed was the synthetic reaction effluent described hereinabove. Steam distillation was carried out at a temperature of 149° C. (300° F.) and crystallization was performed at a temperature of 66° C. (150° F.). The results obtained from this test are presented hereinafter in Table VI.

The results obtained from this run, Run No 14, are presented hereinafter in Table VII.

About 805 gm of water were needed to remove only 3.93 gm of MCHCA in the overhead. Total mass accountability was 96%. The cis-to-trans ratio of 1,4-CHDA changed from 1.37 to 0.75 and the cis-to-trans

TABLE VI

STEAM DISTILLATION AT 149° C. (300° F.) AND CRYSTALLIZATION AT 66° C. (150° F.) WITH RECYCLE CONDENSATE RUN NO. 13

| | Normalized | | | | | Weight Percent | | | | | Weight, gm | | | | |
|---|---|---|---|---|---|---|---|---|---|---|---|---|---|---|---|
| | MCHCA | | 1,4-CHDA | | | MCHCA | | 1,4-CHDA | | | MCHCA | | 1,4-CHDA | | |
| | cis | trans | cis | trans | Others | cis | trans | cis | trans | Water | cis | trans | cis | trans | Water |
| Condensate | 53.26 | 44.91 | 1.04 | 0.65 | 0.07 | 0.032 | 0.246 | 0.006 | 0.004 | 99.44 | 0.61 | 0.50 | 0.01 | 0.01 | 200.7 |
| | 52.76 | 45.41 | 1.17 | 0.63 | 0.04 | 0.529 | 0.439 | 0.012 | 0.006 | 99.01 | 1.06 | 0.88 | 0.02 | 0.01 | 197.0 |
| | 54.92 | 43.30 | 1.12 | 0.62 | 0.03 | 0.412 | 0.313 | 0.008 | 0.005 | 99.26 | 0.82 | 0.62 | 0.02 | 0.01 | 197.2 |
| | 53.23 | 44.78 | 1.33 | 0.62 | 0.04 | 0.494 | 0.402 | 0.012 | 0.006 | 99.09 | 0.95 | 0.77 | 0.02 | 0.01 | 190.6 |
| Filter cake | — | 1.08 | 1.01 | 97.82 | 0.10 | — | 0.92 | 0.89 | 86.63 | 11.47 | — | 2.15 | 2.06 | 201.88 | 26.7 |
| Mother Liquor | 3.46 | 3.15 | 79.04 | 14.33 | 0.03 | 0.38 | 0.33 | 8.52 | 1.55 | 89.22 | 6.43 | 5.65 | 145.29 | 26.50 | 1521.8 |
| Totals | | | | | | | | | | | 9.87 | 10.57 | 147.42 | 228.42 | 2333.9 |
| Starting Materials | | | | | | | | | | | 13.00 | 8.64 | 219.64 | 160.36 | 2500.0 |
| Total Recovery | 94.1% | | | | | | | | | | | | | | |
| Total 1,4-CHDA Recovery | 98.9% | | | | | | | | | | | | | | |
| Total MCHCA Recovery | 94.2% | | | | | | | | | | | | | | |
| Total H₂O Recovery | 93.4% | | | | | | | | | | | | | | |

About 785 gm of water were needed to remove 6.2 gm of MCHCA. The cis-to-trans ratio of 1,4-CHDA changed from 1.37 to 0.65 and the cis-to-trans ratio of the MCHCA changed from 1.50 to 0.93. The cake purity after crystallization at 66° C. (150° F.) was better than that which had been demonstrated with crystallization alone at 66° C. (150° F.). Total mass accountability for this run was about 94%.

ratio of MCHCA changed from 0.45 to 0.49.

TABLE VII

STEAM DISTILLATION AT 149° C. (300° F.) AND CRYSTALLIZATION AT 93° C. (200° F.) WITH cis-MCHCA/trans-MCHCA = 0.45 RUN NO 14

| | Normalized | | | | | Weight Percent | | | | | Weight, gm | | | | |
|---|---|---|---|---|---|---|---|---|---|---|---|---|---|---|---|
| | MCHCA | | 1,4-CHDA | | | MCHCA | | 1,4-CHDA | | | MCHCA | | 1,4-CHDA | | |
| | cis | trans | cis | trans | Others | cis | trans | cis | trans | Water | cis | trans | cis | trans | Water |
| Condensate | 52.34 | 44.48 | 2.15 | 0.97 | 0.07 | 0.201 | 0.165 | 0.008 | 0.004 | 99.62 | 0.40 | 0.33 | 0.02 | 0.01 | 199.2 |
| | 45.40 | 51.42 | 2.32 | 0.83 | 0.04 | 0.229 | 0.250 | 0.012 | 0.004 | 99.51 | 0.46 | 0.51 | 0.02 | 0.01 | 203.1 |
| | — | — | — | — | — | — | — | — | — | — | 0.50 | 0.76 | 0.02 | 0.01 | 200.3 |
| | 41.69 | 54.98 | 2.48 | 0.82 | 0.04 | 0.223 | 0.284 | 0.013 | 0.004 | 99.48 | 0.45 | 0.57 | 0.03 | 0.01 | 202.8 |
| Filter cake | — | 0.53 | 1.27 | 98.17 | 0.04 | — | 0.401 | 0.99 | 77.06 | 21.52 | — | 0.78 | 1.91 | 149.11 | 41.7 |
| Mother Liquor | 1.69 | 3.85 | 67.65 | 26.79 | 0.02 | 0.22 | 0.48 | 8.65 | 3.45 | 87.2 | 3.92 | 8.63 | 155.57 | 61.98 | 1567.6 |
| Totals | | | | | | | | | | | 5.73 | 11.58 | 157.57 | 211.13 | 2414.7 |
| Starting Materials | | | | | | | | | | | 6.11 | 13.44 | 220.07 | 160.67 | 2506.0 |
| Total Recovery | 96% | | | | | | | | | | | | | | |
| Total 1,4-CHDA Recovery | 97% | | | | | | | | | | | | | | |
| Total MCHCA Recovery | 89% | | | | | | | | | | | | | | |
| Total H₂O Recovery | 96% | | | | | | | | | | | | | | |

EXAMPLE 7

In this example, the typical test was conducted with the exception that a blended lot of MCHCA was employed. This blended lot of MCHCA had a cis-to-trans ratio of 0.45. In this run, Run No 14, the steam distillation was performed at a temperature of 149° C. (300° F.) and was followed by crystallization at a temperature of 93° C. (200° F.).

FIG. 3 shows the effect of steam distillation on product purity. It provides a comparison of crystallization to the combination of crystallization and steam distillation. The temperatures of crystallization in degrees Fahrenheit are plotted as abscissae versus the separation factors times 100 as ordinates. As described hereinabove, the separation factor is the ratio of % MCHCA retained on the cake to the % MCHCA in the feed.

As shown by FIG. 3, the combination of crystallization and steam distillation provides a cake purity that is better than that produced by crystallization alone.

The impurities, such as MCHCA, can be purged successfully from a crystallizer via steam distillation, and crystallization of the resulting materials at a temperature of 93° C. (200° F.), or above, results in a cake that contains less than 1% MCHCA and greater than 98% trans-CHDA. Consequently, the purified 1,4-CHDA is substantially all trans-1,4-CHDA, i.e., at least 98 wt % trans-1,4-CHDA. Although the amount of water needed during the purge is substantial, it has been demonstrated hereinabove in Run No 13 that it is possible to recycle the water layer of the condensate back to the crystallizer (and/or presumably to the front end of the process) and still obtain a high-quality product.

The method of the present invention will permit recycle of the total mother liquor, since a substantial amount of impurities are removed and purged from the process through the overhead condensate. Recycle of the mother liquor back to the reactor will facilitate the isomerization of cis-CHDA to trans-CHDA, which is easily crystallized and removed from the product stream.

What is claimed is:

1. A method for purifying 1,4-cyclohexanedicarboxylic acid in an effluent from a reactor wherein purified terephthalic acid is hydrogenated to produce said 1,4-cyclohexanedicarboxylic acid, said effluent comprising said 1,4-cyclohexanedicarboxylic acid, said terephthalic acid, organic impurities comprising at least one of 4-methyl-1-cyclohexanecarboxylic acid and cyclohexanecarboxylic acid, and water, which method comprises passing said effluent into a first crystallizer, said first crystallizer being operated at a temperature that is sufficiently low to permit the formation of crystals of said purified terephthalic acid and yet sufficiently high to permit the formation of a first vapor phase comprising water and at least a portion of said impurities, conducting coextensively in said first crystallizer a first crystallization and first steam distillation, said first crystallization producing a first slurry comprising said crystals of said purified terephthalic acid and a first mother liquor comprising water, 1,4-cyclohexanedicarboxylic acid, and at least a portion of said impurities and said first steam distillation producing said first vapor phase comprising water and at least a portion of said impurities, withdrawing said first vapor phase from said first crystallizer as a first overhead, cooling said first overhead to form a first condensate, separating said first condensate into a first water layer and a first layer of impurities, optionally recycling at least a portion of said first water layer to said first crystallizer, withdrawing said first slurry from said first crystallizer, separating in a first separating means said first slurry into said first mother liquor and said crystals of purified terephthalic acid, passing said first mother liquor into a second crystallizer, said second crystallizer being operated at a temperature that is sufficiently low to permit the formation of crystals of purified 1,4-cyclohexanedicarboxylic acid containing a reduced amount of said impurities and yet sufficiently high to permit the formation of a second vapor phase comprising water and at least a portion of said impurities, conducting coextensively in said second crystallizer a second crystallization and second steam distillation, said second crystallization producing a second slurry comprising said crystals of purified 1,4-cyclohexanedicarboxylic acid and a second mother liquor comprising water and a portion of said impurities and said second steam distillation producing said second vapor phase comprising water and at least a portion of said impurities, withdrawing said second vapor phase from said second crystallizer as a second overhead, cooling said second overhead to form a second condensate, separating said second condensate into a second water layer and a second layer of impurities, optionally recycling at least a portion of said second water layer to said second crystallizer, withdrawing said second slurry from said second crystallizer, separating in a second separating means said second slurry into said second mother liquor and said crystals of purified 1,4-cyclohexanedicarboxylic acid, recycling at least a portion of said second mother liquor to said reactor or said second crystallizer, and recovering said crystals of purified 1,4-cyclohexanedicarboxylic acid.

2. The method of claim 1, wherein said second mother liquor is recycled to said reactor.

3. The method of claim 1, wherein said first crystallizer is operated at a temperature within the range of about 120° C. (248° F.) to about 260° C. (500° F.) and a pressure within the range of about 198 kPa (14 psig) to about 4,693 kPa (666 psig) and said second crystallizer is operated at a temperature within the range of about 66° C. (150° F.) to about 120° C. (248° F.) and a pressure within the range of about 101 kPa (0 psig) to about 198 kPa (14 psig).

4. The method of claim 2, wherein said purified 1,4-cyclohexanedicarboxylic acid is substantially all trans-1,4-cyclohexanedicarboxylic acid.

5. The method of claim 3, wherein said second mother liquor is recycled to said reactor.

6. The method of claim 5, wherein said purified 1,4-cyclohexanedicarboxylic acid is substantially all trans-1,4-cyclohexanedicarboxylic acid.

* * * * *